United States Patent [19]
Arcamone et al.

[11] 4,039,663
[45] Aug. 2, 1977

[54] DAUNOMYCINS, PROCESS FOR THEIR USES AND INTERMEDIATES

[75] Inventors: Federico Arcamone; Aurelio Di Marco; Sergio Penco, all of Milan, Italy

[73] Assignee: Societa' Farmaceutici Italia S.p.A., Milan, Italy

[21] Appl. No.: 560,105

[22] Filed: Mar. 19, 1975

[51] Int. Cl.² .................. A61K 31/71; C07H 11/00
[52] U.S. Cl. .................................. 424/180; 536/4; 536/17; 536/18; 536/115; 536/122
[58] Field of Search ........ 260/210 R, 211 R, 210 AB; 424/180; 536/4, 17, 18

[56] References Cited
U.S. PATENT DOCUMENTS

| 2,949,449 | 8/1960 | Hoffer | 260/210 R |
| 3,356,674 | 12/1967 | Ikeda et al. | 260/210 R |
| 3,427,300 | 2/1969 | Sarett et al. | 260/210 R |
| 3,501,456 | 3/1970 | Shen et al. | 260/210 R |
| 3,524,844 | 8/1970 | Keller-Juslen et al. | 260/210 R |
| 3,686,163 | 8/1972 | Arcamone et al. | 260/210 R |
| 3,803,124 | 4/1974 | Arcamone et al. | 260/210 AB |

Primary Examiner—Johnnie R. Brown
Attorney, Agent, or Firm—Hubbell, Cohen, Stiefel & Gross

[57] ABSTRACT

The known antibiotic daunomycin, and the novel compounds daunomycin-$\beta$-anomer and 4'-epidaunomycin (both $\alpha$- and $\beta$-anomers) are prepared by condensing daunomycinone with reactive novel intermediates which are 1-chloro-2,3,6-trideoxy-3-trifluoroacetamido-4-trifluoroacetoxy-$\alpha$-L-lyxo (or arabino) hexopyranoses.

9 Claims, No Drawings

DAUNOMYCINS, PROCESS FOR THEIR USES AND INTERMEDIATES

BACKGROUND OF THE INVENTION

1. Field of the Invention

The present invention relates to a new process for the synthesis of the known antibiotic daunomycin and its β-anomer, which is a new compound. The invention also relates to the new compounds: 4'-epidaunomycin α-anomer, 4'-epidaunomycin β-anomer and a mixture thereof as well as a process for preparing same. The new processes for preparing daunomycin and 4'-epidaunomycin involve the preparation and use of certain new intermediates which are also included within the invention. The new compounds of the invention are useful in treating certain tumors in animals.

2. Description of the Prior Art

Daunomycin and its aglycone daunomycinone are well known compounds. They are, for example, described and claimed in British Pat. No. 1,033,383, owned by the unrecorded assignee of this application.

SUMMARY OF THE INVENTION

The present invention provides, in one aspect thereof, a new process for preparing daunomycinone glycosides. More specifically, the invention provides a process, which in one embodiment is used for preparing the known compound daunomycin (IV), i.e., 7-O-(3'-amino-2',3',6'-trideoxy-α-L-lyxohexopyranosyl)-daunomycin-one, (IV)

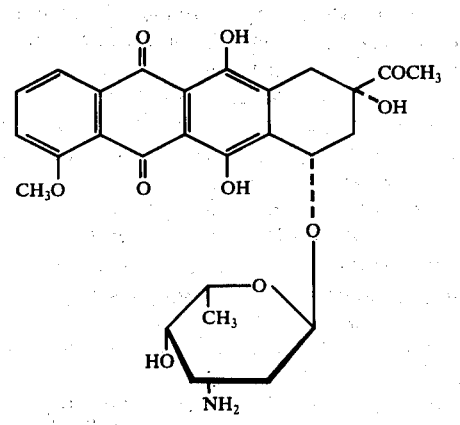

and its β-anomer (V), i.e., 7-O-(3'-amino-2',3',6'-trideoxy-α-L-lyohexopyranosyl)-daunomycinone, which is a novel compound (V)

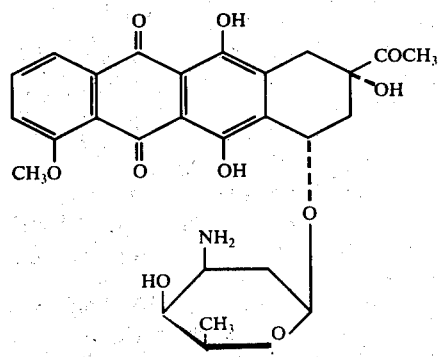

as a mixture of the two anomers as well as each anomer separately, by condensing daunomycinone (I)

(I)

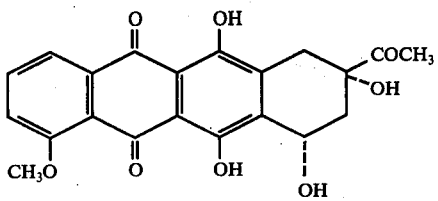

with a reactive protected derivative of daunosamine (II), i.e., 3-amino-2,3,6-trideoxy- L-lyxohexose, (II)

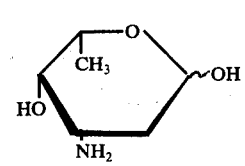

to form the glycosidic linkage after which the α- and β-anomers are separated and the protecting groups, i.e., the trifluoroacetyl groups, on the daunosamine are removed. The reactive protected derivative of daunosamine which is condensed with daunomycinone (I) is the novel intermediate 1-chloro-2,3,6-trideoxy-3-trifluoroacetamido-4-trifluoroacetoxy-α-L-lyxohexopyranone (IIB)

(IIB)

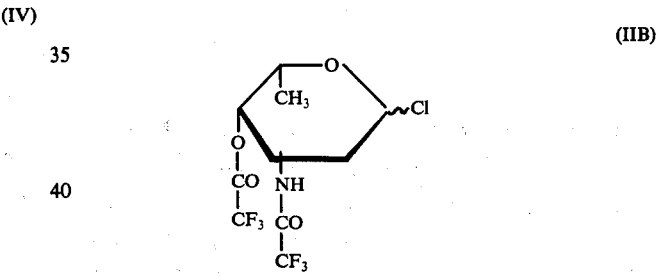

which is obtained from another novel intermediate, 2,3,6-trideoxy-1-trifluoroacetoxy-3-trifluoroacetamido-4-trifluoroacetoxy-L-lyxohexopyranose (IIA)

(IIA),

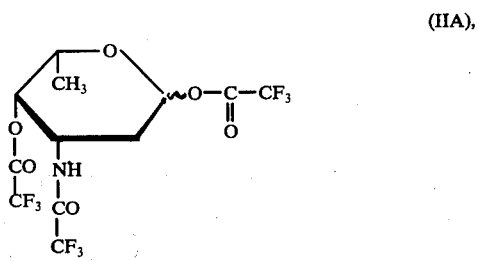

compound (IIA) being prepared by reaction of daunosamine (II) with trifluoroacetic anhydride.

This same process, in another embodiment is used for preparing the novel antibiotics, 4'-epidaunomycin (VI), i.e., 7-O-(3'-amino-2',3',6'-trideoxy-α-L-arabinohexopyranosyl)-daunomycinone (VI)

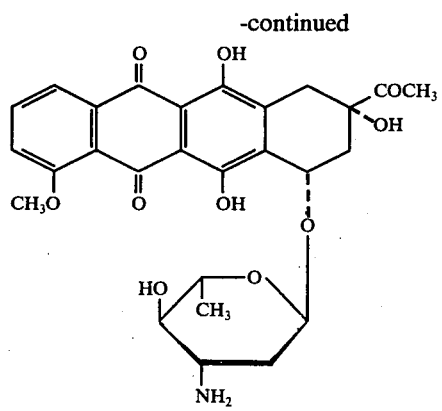

and its β-anomer (VII), i.e., 7-O-(3'-amino-2',3',6'-trideoxy-β-L-arabinohexopyranosyl)-daunomycinone (VII)

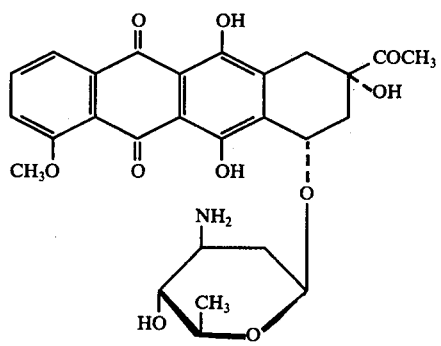

as a mixture of the two anomers as well as each anomer separately. To prepare 4'-epidaunomycin (VI) and its β-anomer (VII), daunomycinone (I) is condensed as described above, with a reactive protected derivative of 4'-epidaunosamine (III), i.e., 3-amino-2,3,6-trideoxy-L-arabinohexose, (III)

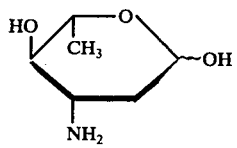

to form the glycosidic linkage, after which the protecting groups on the 4'-epidaunosamine are removed and the α- and β-anomers are separated. The reactive protected derivative of 4'-epidaunosamine which is condensed with daunomycinone (I) is, in this embodiment, also a novel intermediate, namely, 1-chloro-2,3,6-trideoxy-3-trifluoroacetamido-4-trifluoroacetoxy-α-L-arabinohexopyranose (IIIB)

(IIIB)

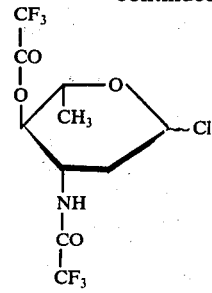

which is obtained from another novel intermediate, 2,3,6-trideoxy-1-trifluoroacetoxy-3-trifluoroacetamido-4-trifluoroacetoxy-L-arabinohexopyranose (IIIA)

(IIIA),

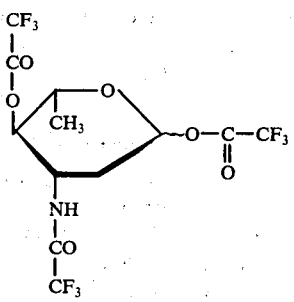

compound (IIIA) being prepared by reaction of 4'-epidaunosamine (III) with trifluoroacetic anhydride. Thus, it is clear that the only essential difference between the two embodiments is the nature of the starting sugar which is reacted (in the form of a reactive protected derivative) with the aglycone (daunomycinone (I)) to form the glycoside. In one embodiment this sugar has the L-lyxose configuration and in the other it has the L-arabinose configuration.

In another aspect, the invention provides the novel antibiotic end products (V) - daunomycin (β-anomer), (VI) 4'-epidaunomycin (α-anomer) and (VII) 4'-epidaunomycin (β-anomer) as well as the novel intermediates (IIA), (IIB), (IIIA) and (IIIB) which are used in the preparation of daunomycin and the novel end products.

In a further aspect, the invention provides methods of using the novel antibiotic end products (V), (VI) and (VIII) in treating various mammalian tumors.

The process of the invention, as stated above, broadly comprises condensing daunomycinone (I) with a derivative of daunosamine (II) or 4'-epidaunosamine (III) to obtain the pharmacologically active glycosides (IV) (daunomycin) and (V) or (VI) and (VII). In practice, the hexose (II) or (III) must first be protected, for example, by forming the trifluoroacetyl derivatives (IIA) and (IIIA) and then converted into reactive derivatives, such as the 1-halides and in particular, the 1-chloro derivatives (IIB) and (IIIB) which are suitable for condensation with daunomycinone (I). After the condensation reaction, the protecting trifluoroacetyl groups are removed. The 4-O-trifluoroacetyl group is firstly removed by treatment with boiling methanol.

The 3-amino groups in the hexoses (II) and (III) must be protected with groups that can subsequently be removed without further decomposition of the products which contain different chemically-sensitive groups The trifluoroacetyl group meets this criterion since it can be readily removed by mild alkaline treatment.

The hexoses (II) and (III) also have to be converted into reactive derivatives which are sufficiently stable to be used in the condensation reaction with daunomycinone (I). The instability of the 1-halo derivatives of 2-deoxysugars is well documented (W. W. Zorbach et al., *Advances in Carbohydrate Chemistry*, 1966, 21, 273). However, according to the invention, it has been found that if the 3-amino and the 1- and 4-hydroxy groups of the hexoses (II) and (III) are protected with trifluoroacetyl groups, the tri-trifluoroacetyl derivatives (IIA) and (IIIA) of the hexoses (II) and (III) can then be reacted with anhydrous hydrogen chloride to give the corresponding 1-chloro-hexoses (IIB) and (IIIB). These latter compounds are solid materials which can be stored for several days under anhydrous conditions.

The tri-trifluoroacetyl derivatives (IIA) and (IIIA) are prepared by reacting, under anhydrous conditions, the hexoses (II) and (III), either as such, or as the hydrochloride, with trifluoroacetic anhydride at about 0° C. in an inert solvent such as diethyl ether.

The 1-chloro-derivatives (IIB) and (IIIB) are then prepared by reacting the tri-trifluoroacetyl derivatives (IIA) and (IIIA), under anhydrous conditions, with anhydrous gaseous hydrogen chloride, in an inert solvent, such as diethyl ether, at a temperature of about 0° C.

The reactive 1-chloro derivative (IIB) or (IIIB) is then reacted with daunomycinone (I) to form the glycoside linkage, after which the protecting trifluoroacetyl groups are removed and the product is separated into the respective α- and β-anomers. Alternatively, the α- and β-anomers can be separated before removal of the protecting trifluoroacetyl groups.

The conditions under which th condensation reaction is effected are modifications of the well known Koenigs-Knorr reaction (Conchie et al., *Advances in Carbohydrate Chemistry*, 1957, 12, 157). This standard reaction contemplates the use of a wide variety of different reaction conditions such as temperature, solvent, catalyst and hydrogen chloride (or bromide) acceptor. However, ordinarily, an optimal set of conditions is necessary to achieve a significant reaction rate. Since the use of the standard KoenigsKnorr reaction conditions with the 1-halo derivatives of 2-deoxy sugars leads to the unwanted formation of the corresponding glycals (Zorbach et al., supra), it is necessary, according to the present invention, to modify those conditions.

The procedure according to the invention therefore comprises reacting daunomycinone (I) with the 1-chloro-N,O-di-trifluoroacetyl derivative (IIB) or (IIIB) of hexose (II) or (III) in an inert organic solvent such as chloroform or methylene dichloride, under mild conditions, in the presence of a catalyst comprising, a mercuric halide, for example, mercuric bromide and a hydrogen chloride acceptor, for example, mercuric oxide, silver carbonate, silver oxide or cadmium carbonate.

The reaction products are then treated firstly with boiling methanol then with a dilute alkali, such as sodium hydroxide to effect removal of both the O- and N-trifluoroacetyl groups and thereby obtain the final products (IV), (V), (VI) and (VII).

PREPARATION OF THE INTERMEDIATE 2,3,6-TRIDEOXY-3-TRIFLUOROACETAMIDO-L-ARABINO-HEXOPYRANOSE 1.0 g of α-methyl-daunosaminide hydrochloride in 25 ml of ethyl ether was treated with 4 ml of $(CF_3CO)_2O$ at 0° C. After 4 hours at room temperature the solution was evaporated to dryness under vacuum and the residue, after complete removal of acidity, was treated with 60 ml of methanol overnight at room temperature. The evaporation of solvent gave 1.3 g of methyl N-trifluoroacetyl daunosaminide: m.p. 108°-109° C; $[\alpha]_D^{23}$ −148° (C0.5 $CHCl_3$). The compound was oxidized to the corresponding C-4 keto-derivative as follows. 2.0 g in 40 ml of $CH_2Cl_2$ were added to a solution of $KIO_4$ (2–3 g), $K_2CO_3$ (0.25 g) and $RuO_2$ (0.12 g) in 40 ml of water. The two phase system was shaken overnight at room temperature; further addition of solid $KIO_4$ (2.3 g), $K_2CO_3$ (0.25 g) and $RuO_2$ (0.12 g) in 6 hours completed the oxidation. The organic layer was separated, filtered, washed, dried and evaporated under reduced pressure to give 1.45 g of methyl 2,3,6-trideoxy-3-trifluoroacetamido-α-L-threo-hexopyranoside-4-ulose: m.p. 77°-80° C; IR ($KB_r$): CO Ketone 1735 $cm^{-1}$, CO amide 1700 $cm^{-1}$; mass spectrum: 255 $m/e$ (M+); pmr ($CDCl_3$): 1.31 (d, J 6.5 $H_z$, $CH_3$—C—5), 1.89 (m, C—2—Hax), 2.88 (m, C—2—Heq), 3.43 (s, $CH_3O$), 4.37 (d, J 6.5 Hz, C—5—H), 4.83 (s, $W_H$ 4.5 $H_z$ C—1 H), 4.95 (two d, J 12.5 $H_z$, J' 6.0 $H_z$, C—3H) and 7.00δ (broad s, NH). The stereo selective reduction with $NaBH_4$ of the keto derivative gave methyl 2,3,6-trideoxy-3-trifluoroacetamido-α-L-arabinopyranoside as follows. The solution of keto derivative (g 1.0) in a mixture of 100 ml of dioxan and 10 ml of water, was treated with 0.1 g of $NaBH_4$ at 5° C. After 10 minutes, the reduction was completed, then the solution was adjusted to pH 4 with resin Dowex W - X2 (H+). The suspension was filtered and evaporation of solvents gave a crude product which was treated several times with methanol in order to remove boric acid. 0.65 G of arabino-derivative were obtained: m.p. 195°-197° C; $[\alpha]_D^{23}$ −110° (c 0.2 MeOH); pmr (DMSO—$d_6$): 1.07 (d, J 6.0 $H_z$, $CH_3$—C—5), 1.5–1.9 (m, C—2—$H_2$), 3.0 (two d [after exchange with $D_2O$], J'=J''=9.5 $H_z$, C—4 H), 3.16 (s, $CH_3O$), 3.44 (two q, J'9.5 $H_z$, J'' 6.0 $H_z$ C—5H), 3.87 (m, C—3H), 4.48 (s, $W_H$ 6.0 C—1 H), 4.84 (d, J 6.5 $H_z$ C—OH) and 8.84δ (broad s, NH). Finally the hydrolysis of the methyl glycoside (1 g) was performed in 20% aqueous acetic acid at 100° C for 2 hours. Evaporation of the acid under vacuum gave a solid product which, by crystallization from $CH_3OH$-$CH_2Cl_2$ (1:3 by vol)-gave 0.6 g of 2,3,6-trideoxy-3-trifluoroacetamido-L-arabinohexopyranose: m.p. 202° C (dec.); $[\alpha]_D^{23}$ −51°, after 2 hours −33.4° (C 0.5 dioxane).

DESCRIPTION OF THE PREFERRED EMBODIMENTS

The following examples are given to illustrate the invention without, however being a limitation thereof. All parts given are by weight unless otherwise indicated.

EXAMPLE 1

PREPARATION OF 2,3,6-TRIDEOXY-1-TRIFLUOROACETOXY3-TRIFLUOROACETAMIDO-4-TRI-FLUOROACETOXY-L-LYOHEXOPYRANOSE (IIA)

One gram of daunosamine (II) hydrochloride was suspended in anhydrous diethyl ether and treated at 0° C with 8 ml of trifluoroacetic anhydride. After allowing the suspension to stand for 2 hours at 0° C and 1 hour at room temperature, the solvent ws removed under reduced pressure and the residue was crystallized from dichloromethane to yield 1.1 g of (IIA), having a m.p. of 132°–134° C. and a mass spectrum m/e 391 (M-44), 322 (M-113).

EXAMPLE 2

PREPARATION OF 1-CHLORO-2,3,6-TRIDEOXY-3-TRIFLUOROACETAMIDO-4-TRI-FLUOROACETOXY-α4-L-LYXOHEXOPYRANOSE (IIB)

0.5 g of (IIA), prepared as in Example 1, was treated in anhydrous diethyl ether at 0° C with anhydrous gaseous hydrogen chloride. After standing at +5° C overnight, the solvent was removed in vacuo to yield (IIB) as a crystalline product. The NMR spectrum in CDCl$_3$ was as follows:

1.22 $\delta$ (d, J = 6.5 Hz, 3H, CH$_3$),
2.05–2.70 $\delta$ (m, 2H, C(2)H$_2$),
4.46 $\delta$ (dq, J = 6.5 Hz and J<1Hz, 1H, C(5)H),
4.60–5.10 $\delta$ (m, 1H, C(3)H),
5.37 $\delta$ (c, W$_H$ = 6.0 Hz, 1H C(4)H),
6.29 $\delta$ (m, W$_H$ = 6.5 Hz, 1H, C(1)H), and
6.37 $\delta$ (broad s, 1H, NH).

EXAMPLE 3

PREPARATION OF DAUNOMYCIN (IV) AND ITS β-ANOMER (V)

300 mg. (0.75 mmol) of finely powdered daunomycinone (I) were dissolved in 75 ml. of anhydrous chloroform and treated with 600 mg. of mercuric oxide, 150 mg. of mercuric bromide and molecular sieve (3A, Merck).

The resulting suspension was stirred for 1 hour and then 600 mg. of (IIB) were added.

The reaction mixture was stirred at room temperature for 64 hours, and then filtered. The solution was then evaporated in vacuo. The residue was taken up in 200 ml. of methanol and refluxed for 15 minutes. The residue which remained after removal of the solvent was chromatographed on a silicic acid column using a mixture of chloroform:benzene:methanol 100:20:3 (by vol.) as the eluent.

In addition to unreacted daunomycinone (I), there were obtained the following:

220 mg. of N-trifluoroacetyl daunomycin (α isomer) m.p. 169°–171° C. (after recrystallization from tetrahydrofuran and hexane), and 20 mg. of N-trifluoroacetyl daunomycin (β isomer), m.p. 138°–140° [α]$_D^{23}$ + 440° (c 0.1 chloroform). 0.20 gm. of N-trifluoroacetyl daunomycin (α isomer) was dissolved in 20 ml. of 0.1 N aqueous sodium hydroxide. The resulting solution, after standing 30 minutes at room temperature was treated with 0.1 N aqueous hydrogen chloride to bring the pH to 8.6, and repeatedly extracted with chloroform.

The combined chloroform extracts were dried over anhydrous sodium sulphate, concentrated to a small volume and acidified to pH 4.5 with 0.1 N methanolic hydrogen chloride to allow crystallization of the daunomycin (IV) hydrochloride. The product was identical in all respects with the product obtained by fermentation (see F. Arcamone et al., Gazzetta Chimica Italiana, 1970, 100, 949), and the yield was practically quantitative. The β-isomer of N-trifluoroacetyl daunomycin can be treated in the same manner to obtain the free β-anomer of daunomycin (V).

EXAMPLE 4

PREPARATION OF 2,3,6-TRIDEOXY-1-TRIFLUOROACETOXY-3-TRIFLUOROACETAMIDO-4-TRI-FLUOROACETOXY-L-ARABINOHEXOPYRANOSE (IIIA)

One gram of 2,3,6-trideoxy-3-trifluoroacetamido-L-arabinohexopyranose was suspended in 20 ml. of anhydrous diethyl ether and treated at 0° C. with trifluoroacetic anhydride. After allowing the suspension to stand for 2 hours at 0° C. and 1 hour at room temperature, the solvent was removed under reduced pressure and the residue crystallized from dichloromethane to yield (IIIA).

EXAMPLE 5

PREPARATION OF 1-CHLORO-2,3,6-TRIDEOXY-3-TRI-FLUOROACETAMIDO-4-TRI-FLUOROACETOXY-α-L-ARABINOHEXOPYRANOSE (IIIB)

Compound (IIIA) obtained as described in Example 4 was treated with anhydrous gaseous hydrogen chloride as described in Example 2 to give a quantitative yield of (IIIB). The NMR spectrum of (IIIB) in CDCl$_3$ was as follows:

1.30 $\delta$ (d, J = 6.0 Hz 3H, CH$_3$),
2.25—2.80 $\delta$ (m, 2H, C(2)H$_2$),
4.20–4.65 $\delta$ (m, 1H, C(5)H),
4.65–5.15 $\delta$ (m, 2H, C(3)H and C(4)H),
6.25 $\delta$ (m, W$_H$ = 6.0 Hz, 1H, C(1)H), and
6.45 $\delta$ (broad s, 1H, NH).

EXAMPLE 6

PREPARATION OF 4'-EPIDAUNOMYCIN (VI) AND ITS β-ANOMER (VII)

A solution of 0.5 gm. of daunomycinone (I) in anhydrous chloroform was treated with 1 gm. of mercuric oxide, 0.25 gm. of mercuric bromide, 10 gm. of molecular sieve (3A, Merck), and 0.5 gm. of (IIIB). The mixture was stirred for 24 hours, freed from solids by filtration, and the filtrate evaporated under vacuum. The residue was taken up in methanol refluxed for 15 minutes, evaporated to dryness and chromatographed on a silicic acid column using a mixture of chloroform:benzene:methanol 10:23:3 (vol.) as the eluent. The main product which was obtained is a mixture, in the ratio 70:30 (weight) of α- and β-7-O-(N-trifluoroacetyl-4'-epidaunosaminyl)-daunomycinone (yield after crystallization from chloroform: 0.3 g). This material, upon treatment with 0.1 N sodium hydroxide as described in Example 3, was converted quantitatively into a mixture of the corresponding α- and β-glycosides (VI) and (VII) in the form of the free bases. The product was separated into the α- and β-anomers by silica gel chromatography using a chloroform:methanol:water 135:20:2 (by vol.) solvent system as the eluent. There was obtained 0.16 gm. of α-anomer-4'-epidaunomycin (VI), $[\alpha]_D^{23}$ +320° (c = 0.045, methanol), m.p. 199°-201°, and 0.06 gm. of β-anomer (VII), m.p. 182°-184°, $[\alpha]_D^{20}$ + 357° (c= 0.02 MeOH).

BIOLOGICAL ACTIVITY

The antitumor activity of the novel antibiotic compounds of the invention, i.e., 4'-epi-daunomycin (VI) and 4'-epidaunomycin, β-anomer, (VII) was evaluated on several transplanted tumors in mice, and in in vitro tests, in comparison with the known antitumor agent daunomycin (IV). The results of these tests are given in the following tables.

BIOLOGICAL ACTIVITY OF 67 4'-EPIDAUNOMYCIN (VI) AND 4'-EPIDAUNOMYCIN β-ANOMER (VII).

Compounds (VI) and (VII) display outstanding biological properties as powerful inhibitors of cell mitosis and proliferative activity in cultured cells in vitro. They also have substantial activity on cell transformation induced by oncogenic viruses, as well as antitumor activity in mice, as shown by an increase in the mean survival time at non-toxic doses in test animals bearing a number of experimental tumors.

ASCITES SARCOMA 180

The tests were carried out on groups of 10 frmale mice (Swiss CD 1). The compounds under examination were administered intraperitoneally in varying doses to the test animals 1 day after intraperitoneal inoculation with 1 × 10⁶ tumor cells per animal. The average survival time is given in Table 1 as a percentage of the survival time of untreated animals, which is arbitrarily designated as 100%. Also given in Table 1 are the number of long term survivors.

TABLE 1

| ACTION ON ASCITES SARCOMA 180 | | | |
|---|---|---|---|
| Compound | Dose (mg/kg) | Average Survival time (%) | Long Term Survivors after 60 days |
| Control | — | 100 | 0 |
| 4'-epidaunomycin α-anomer (VI) | 0.22 | 111.1 | 1/10 |
| | 1.1 | 120.8 | 1/10 |
| | 5.7 | 174.5 | 0/10 |
| 4'-epidaunomycin β-anomer (VII) | 0.26 | 96.6 | 0/10 |
| | 1.3 | 114.8 | 1/10 |
| | 6.7 | 118.6 | 1/10 |

TRANSPLANTED GROSS LEUKEMIA

Inbred C₃H female mice were intravenously inoculated with a suspension of leukemia lymphonodes and spleen cells (2.5 × 10⁶ leukemia cells/mouse) and treated, intravenously, from the first to the fifth day after inoculation with the compounds under examination. The average survival time percentage is given in Table 2.

TABLE 2

| Compound | Daily dosage (mg/kg) | Average Survival Time (%) |
|---|---|---|
| Control | 0 | 100 |
| 4'-epidaunomycin α-anomer (VI) | 1.5 | 115 |
| | 2.25 | 143 |
| | 3 | 162 |
| | 3.75 | 122 |

TABLE 2-continued

| Compound | Daily dosage (mg/kg) | Average Survival Time (%) |
|---|---|---|
| | 4.5 | 120 |
| 4'-epidaunomycin β-anomer (VII) | 1.5 | 106 |
| | 2.25 | 102 |
| | 3 | 121 |

TESTS IN VITRO ON THE FORMATION OF FOCI BY MOLONEY SARCOMA VIRUS (MSV.).

The test compounds were evaluated on mouse embryo fibroblast cultures infected with MSV. After a treatment of three days, the inhibiting doses (ID₅₀) were evaluated on cell proliferation and onn MSV foci formation. The results obtained are given in Table 3.

TABLE 3

Effect of compounds (VI and (VII) on foci formation and on cell proliferation in cultured mice fibroblasts infected with Moloney Sarcoma Virus. (3 days treatment)

TABLE 3

| Compound | Dose (μg/ml) | Foci Formation (% of controls) | Foci Formation ID₅₀ (μg/ml) (A) | Cell Proliferation (% of controls) | Cell Proliferation ID₅₀ (μg/ml) (B) | B/A |
|---|---|---|---|---|---|---|
| 4'-epidaunomycin α-anomer (VI) | 0.0062 | 51 | | 75 | | |
| | 0.025 | 0 | 0.006 | 23 | 0.013 | 2.1 |
| | 0.1 | 0 | | 14 | | |
| | 0.4 | 0 | | 1 | | |
| 4'-epidaunomycin β-anomer (VII) | 0.0062 | 48 | | 87 | | |
| | 0.025 | 44 | 0.01 | 80 | 0.064 | 6.4 |
| | 0.1 | 5 | | 28 | | |
| | 0.4 | 0 | | 14 | | |
| Daunomycin (IV) | | | 0.006 | | 0.0086 | 1.4 |

TABLE 4

Tests in vitro on the effect of compounds (VI) and (VII) on the micotic index and the proliferative activity of cultured HeLa cells at different exposure times. The results in Table 4 are expressed as a percent of the untreated controls. The ID₅₀ represents the dose which gives a 50% inhibition of colonies.

TABLE 4

| Compound | Dose (μg/ml) | Micotic Index 2h | Micotic Index 4h | Micotic Index 8h | Colony Counts 2h | Colony Counts 8h | Colony Counts 24h |
|---|---|---|---|---|---|---|---|
| 4'-epidaunomycin α-anomer (VI) | 0.025 | 226* | 100 | 117 | 113 | 88 | 48 |
| | 0.05 | 189* | 103 | 122 | 115 | 56 | 23 |
| | 0.1 | 79 | 140 | 0 | 77 | 23 | 3 |
| | ID₅₀ | | | | 0.16 | 0.056 | 0.027 |
| 4'-epidaunomycin β-anomer (VII) | 0.25 | 137 | 103 | 85 | 108 | 86 | 70 |
| | 0.5 | 95 | 67 | 88 | 101 | 37 | 18 |
| | 1 | 52 | 40 | 0 | 98 | 17 | 6 |
| | ID₅₀ | | | | >1 | 0.47 | 0.33 |
| Daunomycin IV | ID₅₀ | | | | 0.098 | 0.036 | 0.021 |

*Metaphasic block.

TESTS IN VITRO ON THE CARDIOTOXIC ACTIVITY

The cardiotoxic activity of compound (VI) was evaluated in vitro on single myocardial cells isolated by trypsinization from the hearts of newborn mice (Necco A., Dasdia T. IRCS, 2: 1293, 1974). After 3-4 days, the cell cultures, showing clusters of beating cells, are studied both as to frequency and rhythym.

The cardiotoxic activity of compound (VI) - 4'-epidaunomycin, α-anomer, was found to be lower than that of daunomycin (IV).

Variations and modifications, can of course, be made without departing from the spirit and scope of the invention.

Having thus described our invention, what we desire to secure by Letters Patent and hereby claim is:

1. A mixture of the α- and β-anomers of 4'epidaunomycin wherein the α-anomer comprises about 70% by weight and the β-anomer comprises about 30% by weight.

2. A 2,3,6-trideoxy-1-trifluoroacetoxy-3-trifluoroacetamido-4-trifluoroacetoxy-L-hexose selected from the group consisting of 2,3,6-trideoxy-1-trifluoroacetoxy-3-trifluoroacetamido-4-trifluoroacetoxy-L-lyxohexopyranose and 2,3,6-trideoxy-1-trifluoroacetoxy-3-trifluoroacetamido-4-trifluoroacetoxy-L-arabinohexopyranose.

3. A compound according to claim 2 which is 2,3,6-trideoxy-1-trifluoroacetoxy-3-trifluoroacetamido-4-trifluoroacetoxy-L-lyxohexopyranose.

4. A compound according to claim 2 which is 2,3,6-trideoxy-1-trifluoroacetoxy-3-trifluoroacetamido-4-trifluoroacetoxy-L-arabinohexopyranose.

5. A 1-chloro-2,3,6-trideoxy-3-trifluoroacetamido-4-trifluoroacetoxy-L-hexose selected from the group consisting of 1-chloro-2,3,6-trideoxy-3-trifluoroacetamido-4-trifluoroacetoxy-α-L-lyxohexopyranose and 1-chloro-2,3,6-trideoxy-3-trifluoroacetamido-4-trifluoroacetoxy-α-L-arabinohexopyranose.

6. A compound according to claim 5 which is 1-chloro-2,3,6-trideoxy-3-trifluoroacetamido-4-trifluoroecetoxy-α-L-lyxohexopyranose.

7. A compound according to claim 5 which is 1-chloro-2,3,6-trideoxy-3-trifluoroacetamido-4-trifluoroacetoxy-α-L-arabinohexopyranose.

8. A method of inhibiting the growth of a tumor selected from the group consisting of Moloney Sarcoma Virus, Sacroma 180 Ascites and gross transplantable leukemia which comprises administering to a host afflicted with said tumor an amount of the mixture of claim 1 sufficient to inhibit the growth of said tumor, together with an inert, pharmaceutically acceptable carrier.

9. A method according to claim 8 wherein the compound is administered intravenously.

* * * * *

Sheet 1 of 2

UNITED STATES PATENT OFFICE
CERTIFICATE OF CORRECTION

Patent No. 4,039,663  Dated August 2, 1977

Inventor(s) Federico Arcamone et al

It is certified that error appears in the above-identified patent and that said Letters Patent are hereby corrected as shown below:

Column 1, line 51: "trideoxy-α-L-" should read -- trideoxy-β-L- --.

Column 2, line 32: "none (IIB)" should read -- nose (IIB) --.

Column 4, line 50: "(VIII)" should read -- (VII) --.

Column 5, line 49: "KoenigsKnorr" should read -- Koenigs-Knorr --.

Column 7, line 4: "-TRIFLUOROACETOXY3-" should read -- -TRIFLUOROACETOXY-3- --; line 6: "-LYOHEXOPYRANOSE" should read -- -LYXOHEXOPYRANOSE --; line 23: "FLUOROACETOXY-α4" should read -- FLUOROACETOXY-α- --.

Column 8, line 62: "10:23:3" should read -- 10:20:3 --.

Column 9, line 20: "BIOLOGICAL ACTIVITY OF 67" should read -- BIOLOGICAL ACTIVITY OF --; line 33: "frmale" should read -- female --; after Table 1: should read -- 6/10 of the test animals died as a result of drug toxicity --.

Column 10, Table 3, column 1: "4'-epidaunomycinα-" should read -- 4'-epidaunomycin α- --.

UNITED STATES PATENT OFFICE
CERTIFICATE OF CORRECTION

Patent No. 4,039,663     Dated  August 2, 1977

Inventor(s) Federico Arcamone et al

It is certified that error appears in the above-identified patent and that said Letters Patent are hereby corrected as shown below:

Column 12, line 3 of claim 6: "ecetoxy-" should read -- acetoxy- --.

Signed and Sealed this

First Day of November 1977

[SEAL]

Attest:

RUTH C. MASON
Attesting Officer

LUTRELLE F. PARKER
Acting Commissioner of Patents and Trademarks